(12) United States Patent
Pan

(10) Patent No.: US 10,825,994 B2
(45) Date of Patent: Nov. 3, 2020

(54) ORGANIC LIGHT EMITTING DEVICE AND PREPARATION METHOD THEREOF

(71) Applicant: Wuhan China Star Optoelectronics Technology Co., Ltd., Hubei (CN)

(72) Inventor: Biao Pan, Wuhan (CN)

(73) Assignee: Wuhan China Star Optoelectronics Technology, Ltd., Wuhan (CN)

( * ) Notice: Subject to any disclaimer, the term of this patent is extended or adjusted under 35 U.S.C. 154(b) by 157 days.

(21) Appl. No.: 15/552,221

(22) PCT Filed: Jun. 22, 2017

(86) PCT No.: PCT/CN2017/089607
§ 371 (c)(1),
(2) Date: Aug. 18, 2017

(87) PCT Pub. No.: WO2018/166096
PCT Pub. Date: Sep. 20, 2018

(65) Prior Publication Data
US 2018/0331302 A1      Nov. 15, 2018

(30) Foreign Application Priority Data
Mar. 16, 2017   (CN) .......................... 2017 1 0155875

(51) Int. Cl.
*H01L 51/00*     (2006.01)
*C09K 11/06*     (2006.01)
(Continued)

(52) U.S. Cl.
CPC ........ *H01L 51/0072* (2013.01); *C07D 235/18* (2013.01); *C07D 403/10* (2013.01);
(Continued)

(58) Field of Classification Search
CPC .................................................... C07D 235/18
See application file for complete search history.

(56) References Cited

U.S. PATENT DOCUMENTS 7,133,032 B2 *  11/2006  Cok ...................... G06F 3/0412
                                                                345/175
2009/0011278 A1 *  1/2009  Choi ................... H01L 51/5234
                                                                428/690
(Continued)

FOREIGN PATENT DOCUMENTS

CN       101863914 A     10/2010
CN       103804301 A      5/2014
(Continued)

OTHER PUBLICATIONS

Zhou et al., English machine translation of CN103804301 (Year: 2014).*

*Primary Examiner* — Peter F Godenschwager
(74) *Attorney, Agent, or Firm* — Nelson Mullins Riley & Scarborough LLP; Kongsik Kim, Esq.

(57) ABSTRACT

The present invention relates to a display technical field, especially to an organic light emitting device which includes from the bottom to the top: a substrate, an anode layer, a hole injection layer, a hole transport layer, an exciton blocking
(Continued)

layer, an organic light emitting layer, an electron transport layer, an electron injection layer and a cathode layer; the material of the organic light emitting layer includes benzimidazole derivative as illustrated in Formula 1,

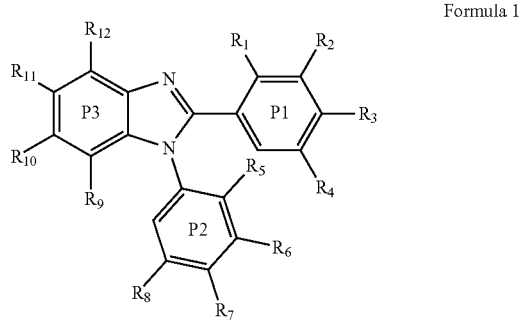

Formula 1 wherein P1, P2 and P3 are benzene rings, and at least one of $R_1 \sim R_{12}$ is a substituent having hole transport ability. The present invention further provides preparing methods for the organic light emitting layer and device.

6 Claims, 6 Drawing Sheets

(51) Int. Cl.
    *C07D 403/10*     (2006.01)
    *H01L 51/56*     (2006.01)
    *C07D 235/18*     (2006.01)
    *H01L 51/50*     (2006.01)
    *H01L 51/52*     (2006.01)

(52) U.S. Cl.
    CPC .............. *C09K 11/06* (2013.01); *H01L 51/56* (2013.01); *C09K 2211/1018* (2013.01); *H01L 51/001* (2013.01); *H01L 51/5004* (2013.01); *H01L 51/5016* (2013.01); *H01L 51/5056* (2013.01); *H01L 51/5072* (2013.01); *H01L 51/5088* (2013.01); *H01L 51/5096* (2013.01); *H01L 51/5221* (2013.01); *H01L 2251/301* (2013.01); *H01L 2251/552* (2013.01)

(56) References Cited

U.S. PATENT DOCUMENTS

| | | | |
|---|---|---|---|
| 2013/0075705 A1 | 3/2013 | Takasu et al. | |
| 2016/0148560 A1* | 5/2016 | Tsai | H01L 51/504 345/690 |
| 2016/0315274 A1* | 10/2016 | Lennartz | H01L 51/0055 |
| 2017/0162793 A1* | 6/2017 | Huang | C09K 11/025 |

FOREIGN PATENT DOCUMENTS

| | | |
|---|---|---|
| CN | 103804360 A | 5/2014 |
| CN | 104650041 A | 5/2015 |
| CN | 105349137 A | 2/2016 |
| TW | I564298 B | 1/2017 |
| WO | 2014017094 A1 | 1/2014 |

* cited by examiner

US 10,825,994 B2

ORGANIC LIGHT EMITTING DEVICE AND PREPARATION METHOD THEREOF

CROSS-REFERENCE TO RELATED APPLICATION

This application is the U.S. national phase of PCT Application No. PCT/CN2017/089607 filed on Jun. 22, 2017, which claims priority to CN Patent Application No. 201710155875.2 filed on Mar. 16, 2017, the disclosures of which are incorporated in their entirety by reference herein.

TECHNICAL FIELD

The present invention belongs to a flexible display technical field, more particularly, to a preparation of an organic light emitting device.

BACKGROUND ART

In 1987, professor, Ching W. Tang, and Vanslyke adopted an ultrathin film technique which used a transparent conducting film as anode, AlQ$_3$ as a light emitting layer, triarylated amine as a hole transport layer and Mg/Ag alloy as cathode to prepare a double-layered organic electroluminescent device (*Appl. Phys. Lett.*, 1987, 52, 913). In 1990, Burroughes et al found an OLED in which conjugated polymer PPV is a light emitting layer (*Nature*. 1990, 347, 539), since then an upsurge for research on OLED is inspired within all over the world.

Most we see in daily life is fluorescence phenomenon due to the effect of spin limit. The initial technical research of OLED mainly focused on fluorescent devices. However, according to the principle of spin quantum statistics, the greatest internal quantum efficiency of a fluorescent electroluminescent device is only 25%, while that of a phosphor electroluminescent device may reach to 100%. Hence, after Forrest and Thompson et al (*Appl. Phys. Let.*, 1999, 75, 4) doped a green phosphor material Ir(ppy)$_3$ into a main body material of 4,4'-N,N'-bicarbazole-biphenyl (CBP) with a concentration of 6 wt % to obtain that the greatest external quantum efficiency (EQE) of the green light OLED reaches to 8% in 1999, which breaks through the principle limit of an electrofluorescent device, people give great concern on phosphor light emitting materials. Thereafter, electrophosphorescent materials and phosphor devices are always hot spots of the OLED research.

Since the lifetime of triplet exciton is comparatively long, in order to restrain annihilation process of the triplet-triplet exciton in a device with a high concentration, an electrophosphorescent devices generally adopt a host-object doped device structure, that is, a phosphorescent host material doped with a certain percent of a phosphorescent object material is used as a light emitting layer. A light emitting mechanism of the device is an energy transfer pattern between a host and an object or a direct capture pattern of carriers on an object. The former is that the excitons are formed on the phosphorescent host, then the energy is transferred to the phosphorescent object to be finally emitted in a form of light. As a result, the design for the phosphorescent host material is highly required. At present, the currently commercialized OLED has gradually occupied display and illumination industries. Efficiencies of red and green phosphorescent host materials and the stabilities thereof both have basically satisfied the requirements for display and illumination, however, a blue phosphorescent material is always a bottleneck for an organic electroluminescent device.

In general, the design principle for the blue phosphorescent host material includes the following: 1. a triplet energy level is larger than that of an object to realize effective energy transfer of the exciton; 2. there is a HOMO and LUMO energy level matching a neighboring layer to reduce an energy barrier for the injection of the carrier; 3. there is a matched hole and electron mobility; and 4. good thermal stability and film forming ability. In order to simultaneously realize these three different requirements in the same molecule, researchers had conducted a plurality of meaningful attempts and developed different kinds of phosphorescent luminous host materials. Wherein a benzimidazolyl group shows a comparatively strong electron withdrawing characteristic and a comparatively strong modification, and has preferable electron injection and transport characteristics, so as to be suitable for a blue phosphorescent host material.

In 2011, the research group of Ken-Tsung Wong, a professor of Taiwan University, reported a group of phosphorescent host materials for directly connecting the third bit of 9-phenylcarbazole with benzimidazole, the structure thereof is as shown in FIG. 1). The result shows that the conjugation degree of the molecules can be effectively changed and the excitation state energy level of the molecules can be adjusted by changing the connection position of benzimidazole (reference [1] Chen Y M, Hung W Y, You H W, et al. Carbazole-benzimidazole hybrid bipolar host materials for highly efficient green and blue phosphorescent OLEDs. Journal of Materials Chemistry, 2011, 21(38): 14971~14978.).

Fig. (1)

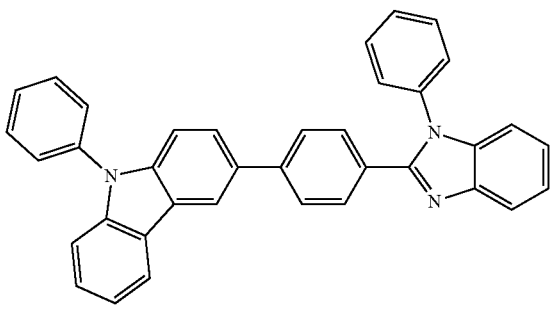

CZbCBI

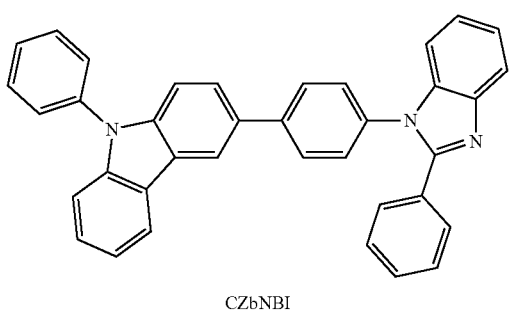

CZbNBI

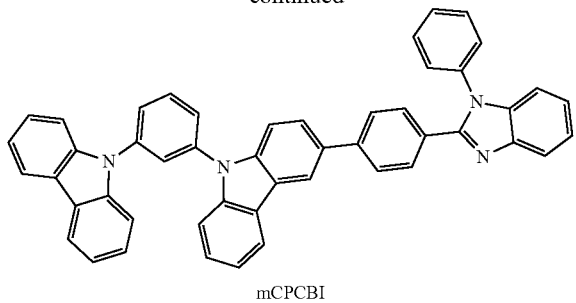

mCPCBI

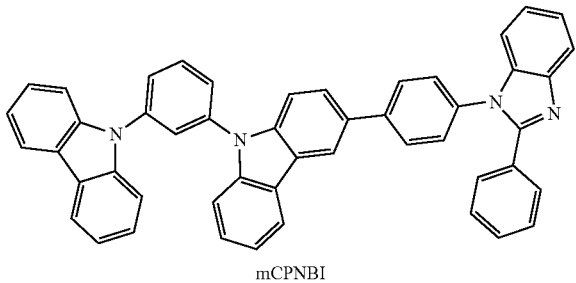

mCPNBI

However, it should be noticed at the same time that the light emitting efficiency of the series of the materials is still comparatively low, wherein the device with a main body of mCPNBI obtains the greatest blue light emitting efficiency, but the greatest external quantum efficiency, the current efficiency and the power efficiency are still only 16.3%, 35.7 cd/A and 23.3 lm/W, which still cannot satisfy the requirements for display and illumination.

SUMMARY

Aiming at the above defects or improvement requirements in the prior art, the present invention provides a benzimidazole based derivative, preparing method and application thereof, and the purpose thereof lies in that solving technical problems of poor stability and low efficiency of a blue phosphorescent device in the prior art by synthesizing benzimidazole based derivatives using a simple and implementable synthesizing scheme and applying the same to an electroluminescent device.

In order to solve the problems existing in the prior art, the present invention provides an organic light emitting device which includes from the bottom to the top: a substrate, an anode layer, a hole injection layer, a hole transport layer, an exciton blocking layer, an organic light emitting layer, an electron transport layer, an electron injection layer and a cathode layer; wherein the material of the organic light emitting layer includes benzimidazole derivative as illustrated in Formula 1,

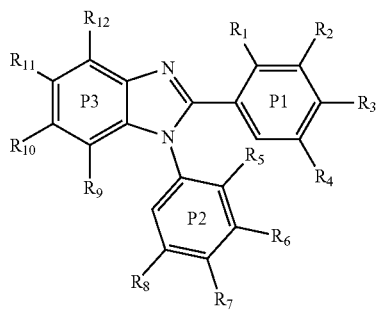

Formula 1 wherein, P1, P2 and P3 are benzene rings, and at least one of $R_1 \sim R_{12}$ is a substituent having hole transport ability.

Wherein the substituent having hole transport ability is selected from a heterocyclic group in which the number of carbon atoms is 5~65, or an aromatic group, a polycyclic group, an arylene group or an arylene heterocyclic group in which the number of carbon atoms is 6~65.

Wherein $R_1 \sim R_{12}$ are selected from a hydrogen group, a phenyl group, a p-tolyl, a biaza-9-carbazolyl, a triphenyl silyl, a p-triphenylamino, a dimethyl p-triphenylamino, a ditert-butyl carbazolyl, a 1-naphthalene substituted p-triphenylamino, a 2-naphthalene substituted p-triphenylamino, a 3,6-ditert-butyl carbazolyl phenyl, a di3,6-ditert-butyl carbazolyl phenyl, a p-triphenylamino, a dimethyl p-triphenylamino, a 1-naphthalene substituted p-triphenylamino, a 2-naphthalene substituted p-triphenylamino, a 2-dibenzothiophene, a 3-dibenzothiophene, a 4-dibenzothiophene and a m-terphenyl.

Wherein the organic light emitting layer further includes a dopant which is bis(4,6-difluorophenylpyridinato-N,C2)picolinatoiridium, or bis(2-phenyl-benzothiazole-C2,N)(acetylacetonate)iridium (III); and the mass fraction that the dopant occupies the organic light emitting layer is 0.5~7 wt %.

Wherein the mass fraction that the dopant bis(2-phenyl-benzothiazole-C2,N)(acetylacetonate)iridium (III)) occupies the organic light emitting layer is 0.5~5 wt %.

Wherein the material of the anode layer is a semiconductor conducting film; the material of the hole injection layer is molybdenum oxide; the material of the hole transport layer is N,N'-diphenyl-N,N'-(1-naphthyl)-1,1'-biphenyl-4,4'-diamine or 4,4'-cyclohexyl di[N,N-di(4-methylphenyl)phenylamine]; the material of the exciton blocking layer is N,N'-dicarbazole-3,5-benzene (mCP) or 4,4',4"-tris(carbazole-9-yl)triphenylamine; the material of the electron transport layer is 1,3,5-tris[(3-pyridinyl)-3-phenyl]benzene; the material of the electron injection layer is LiF; and the cathode layer is Al.

The present invention further provides a preparing method for an organic light emitting device which includes:
  forming an anode layer on a substrate;
  sequentially forming a hole injection layer, a hole transport layer and an exciton blocking layer on the anode layer using a vacuum thermal evaporation method,
  forming an organic light emitting layer which includes benzimidazole derivative as illustrated in Formula 1 on the exciton blocking layer using a vacuum thermal evaporation method,

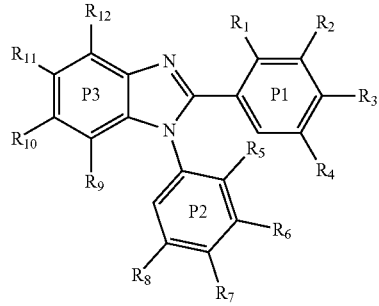

Formula 1 wherein P1, P2 and P3 are benzene rings, and at least one of $R_1 \sim R_{12}$ is a substituent having hole transport ability;

and forming an electron transport layer, an electron injection layer and a cathode layer on the organic light emitting layer using a vacuum thermal evaporation method.

Wherein the substituent having hole transport ability is selected from a heterocyclic group in which the number of carbon atoms is 5~65, or an aromatic group, a polycyclic group, an arylene group or an arylene heterocyclic group in which the number of carbon atoms is 6~65.

Wherein $R_1$~$R_{12}$ are selected from a hydrogen group, a phenyl group, a p-tolyl, a biaza-9-carbazolyl, a triphenyl silyl, a p-triphenylamino, a dimethyl p-triphenylamino, a ditert-butyl carbazolyl, a 1-naphthalene substituted p-triphenylamino, a 2-naphthalene substituted p-triphenylamino, a 3,6-ditert-butyl carbazolyl phenyl, a di3,6-ditert-butyl carbazolyl phenyl, a p-triphenylamino, a dimethyl p-triphenylamino, a 1-naphthalene substituted p-triphenylamino, a 2-naphthalene substituted p-triphenylamino, a 2-dibenzothiophene, a 3-dibenzothiophene, a 4-dibenzothiophene and a m-terphenyl.

Wherein the organic light emitting layer further includes a dopant which is bis(4,6-difluorophenylpyridinato-N,C2)picolinatoiridium, or bis(2-phenyl-benzothiazole-C2,N)(acetylacetonate)iridium (III); and the mass fraction that the dopant occupies the organic light emitting layer is 0.5~7 wt %.

Advantageous Effects

Since a benzimidazolyl group shows a comparatively strong electron withdrawing characteristic, a comparatively strong modification, and has preferable electron injection and transport characteristics, it suitable for being a phosphorescent host material.

Thus, the present invention has the following advantages:

(1) the benzimidazole based derivatives provided by the present invention has advantages of a simple structure and a high triplet energy level with respect to the double carbazole substituted host material, which can implement effective energy transfer of triplet exciton from a host to an object;

(2) the benzimidazole based derivatives provided by the present invention has a balanced carrier mobility, which can implement effective recombination of holes and electrons in a light emitting area and increase light emitting efficiency of a device;

(3) the benzimidazole based derivatives provided by the present invention has a comparatively small steric hindrance, which may notably improve glass transition temperature and heat stability and can improve the usage lifetime of a light emitting device;

(4) the blue phosphorescent OLED device, which uses benzimidazole based derivatives as a light emitting layer, provided by the present invention, has excellent performance and the current efficiency, the power efficiency and the external quantum efficiency thereof all can achieve a relatively high level of performances of current blue phosphorescent devices;

(5) the white phosphorescent OLED device, which uses mNBICz as a light emitting layer, provided by the present invention, has excellent performance, and the current efficiency, the power efficiency and the external quantum efficiency thereof all can achieve a relatively high level of performances of current white phosphorescent devices; and (6) the benzimidazole based derivatives provided by the present invention may be applied to display and illumination fields.

BRIEF DESCRIPTION OF THE DRAWINGS

The above and other aspects, features and advantages of the embodiments of the present invention will become more apparent from the following description, taken in conjunction with the accompanying drawings in which.

DETAILED DESCRIPTION OF EXEMPLARY EMBODIMENTS

Embodiments of the present invention will be described in detail below by referring to the accompany drawings. However, the present invention can be implemented in numerous different forms, and the present invention should not be explained to be limited to the particular embodiments set forth herein. Instead, these embodiments are provided for explaining the principle and actual application of the present invention, thus other skilled in the art can understand various embodiments and various amendments which are suitable for specific intended applications of the present invention.

In the organic light emitting device provided by the present invention, the organic light emitting layer thereof is prepared by a highly effective electrophosphorescent material, and accordingly technical problems of poor stability and low efficiency of a blue phosphorescent device in the prior art are solved.

Embodiment 1

Figure 1:
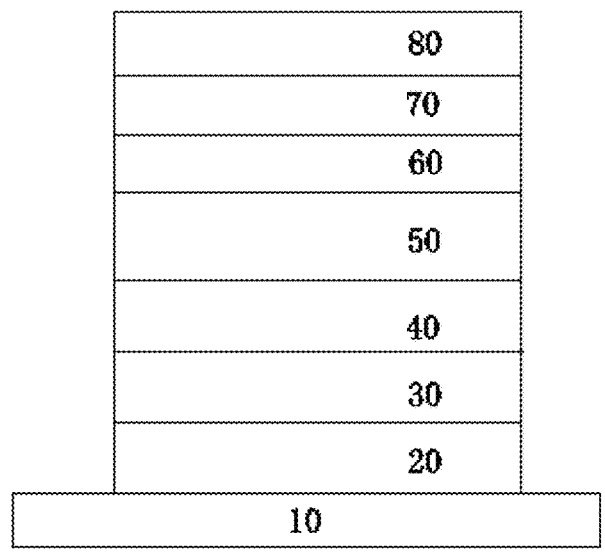
FIG. 1 is a schematic diagram of a structure of an organic light emitting device of embodiment 1 of the present invention.

As shown in FIG. 1, the present embodiment provides an organic light emitting device which includes from the bottom to the top: an anode layer 10, a hole injection layer 20, a hole transport layer 30, an exciton blocking layer 40, an organic light emitting layer 50, an electron transport layer 60, an electron injection layer 70 and a cathode layer 80.

The material of the anode layer is a semiconductor conducting film (ITO); the material of the hole injection layer is molybdenum oxide ($MoO_3$); the material of the hole transport layer is N,N'-diphenyl-N,N'-(1-naphthyl)-1,1'-biphenyl-4,4'-diamine (NPB) or 4,4'-cyclohexyl di[N,N-di(4-methylphenyl)phenylamine] (TAPC); the material of the exciton blocking layer is N,N'-dicarbazolyl-3,5-benzene (mCP); the material of the electron transport layer is 1,3,5-tris[(3-pyridinyl)-3-phenyl]benzene (TmPyPB); the material of the electron injection layer is LiF; and the cathode layer is Al.

Wherein, the material of the organic light emitting layer includes benzimidazole derivative illustrated in Formula 1. Preferably, in order to restrain the annihilation process of the triplet-triplet exciton in a device with a high concentration, an electrophosphorescent device is generally adopted with a host-object doped device structure. Thus, the electrophosphorescent device further includes dopants as an object material in addition to benzimidazole derivative as a host material, which are evaporated together in a certain proportion. The dopant may be, for example, bis(4,6-difluorophenylpyridinato-N, C2)picolinatoiridium (FIrpic).

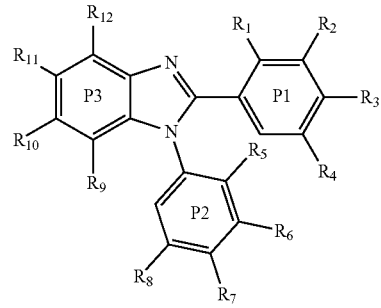

Formula 1

Wherein, P1, P2 and P3 are benzene rings, and at least one of $R_1$~$R_{12}$ is a substituent having hole transport ability, and the rest thereof may be H.

Theoretically, substitution reaction may be occurred at any positions of benzene rings P1, P2 and P3 to modify a substituent having hole transport ability. In fact, once a substituent having hole transport ability is formed on one benzene ring, probability that substitution reactions of other substituents occurred on the benzene ring is lowered.

If a two sites substitution is formed, on one hand, delocalization distribution range of electrons thereof may increase, and the triplet thereof is lowered; on the other hand, performing modification on the same benzene ring may increase steric hindrance and affect the stability of the structure thereof. Hence, more situations on P1, P2 or P3 in actual application are that there is only one other substituent except for H due to substitution steric hindrance and electron cloud structure limit.

Specifically, $R_1$~$R_{12}$ are each independently H or a heterocyclic group in which the number of carbon atoms is 5~65, or the following groups in which the number of carbon atoms is 6~65: an aromatic group, a polycyclic group, an arylene group or an arylene heterocyclic group.

For example, $R_1$~$R_{12}$ may be any one substituent particularly selected from Table 1.

TABLE 1

Structures and names of respective substituents $R_1$~$R_{12}$

| Serial Number of Structural Formula | Substituent Structure | Substiutent name |
|---|---|---|
| 1 | H— | hydrogen group |
| 2 | —⌬ | phenyl group |
| 3 | —⌬— | p-tolyl |

TABLE 1-continued
Structures and names of respective substituents R$_1$~R$_{12}$
| Serial Number of Structural Formula | Substituent Structure | Substituent name |
|---|---|---|
| 4 | 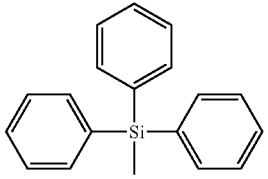 [SMILES: C[Si](c1ccccc1)(c1ccccc1)c1ccccc1] | triphenylsilyl |
| 5 | 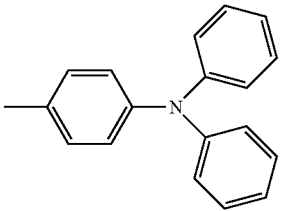 [SMILES: Cc1ccc(N(c2ccccc2)c2ccccc2)cc1] | p-triphenylamino |
| 6 | 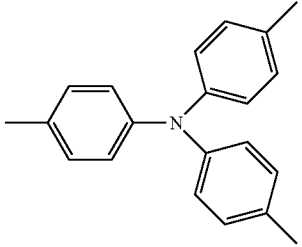 | dimethyl p-triphenylamino |
| 7 | 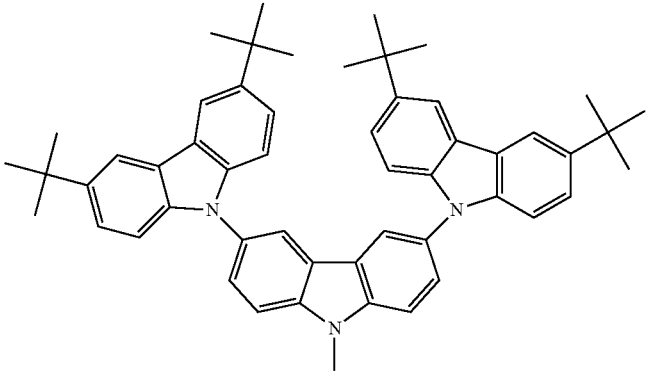 [SMILES: Cn1c2ccc(-n3c4ccc(C(C)(C)C)cc4c4cc(C(C)(C)C)ccc43)cc2c2cc(-n3c4ccc(C(C)(C)C)cc4c4cc(C(C)(C)C)ccc43)ccc21] | ditert-butyl carbazolyl, |
| 8 | 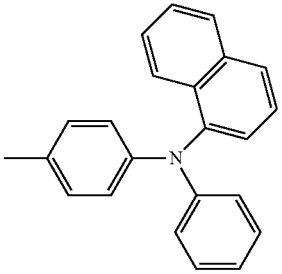 [SMILES: Cc1ccc(N(c2ccccc2)c2cccc3ccccc23)cc1] | 1-naphthalene substituted p-triphenylamino |

TABLE 1-continued
Structures and names of respective substituents $R_1$~$R_{12}$
| Serial Number of Structural Formula | Substituent Structure | Substiutent name |
|---|---|---|
| 9 | 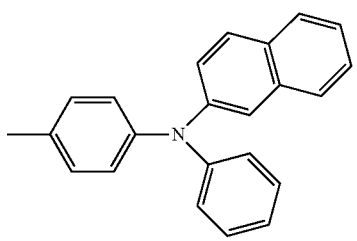 [SMILES: Cc1ccc(N(c2ccccc2)c2ccc3ccccc3c2)cc1] | 2-naphthalene substituted p-triphenylamino |
| 10 | 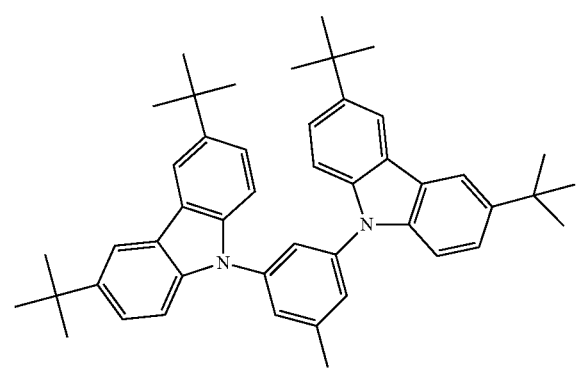 [SMILES: Cc1cc(-n2c3ccc(C(C)(C)C)cc3c3cc(C(C)(C)C)ccc32)cc(-n2c3ccc(C(C)(C)C)cc3c3cc(C(C)(C)C)ccc32)c1] | 3,6-ditert-butyl carbazolyl phenyl |
| 11 | 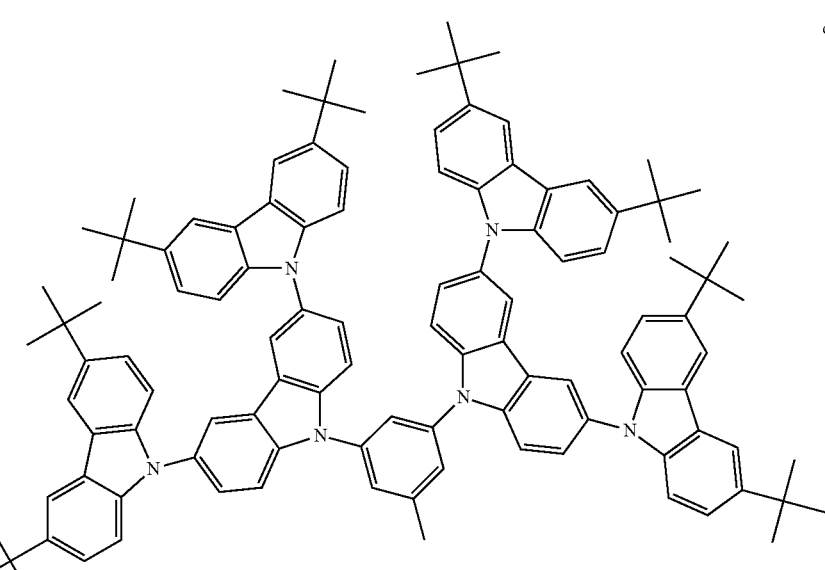 | di3,6-ditert-butyl carbazolyl phenyl |
| 12 | 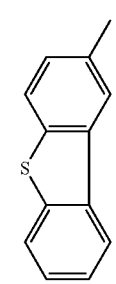 | 2-dibenzothiophene |

TABLE 1-continued

Structures and names of respective substituents $R_1$~$R_{12}$

| Serial Number of Structural Formula | Substituent Structure | Substiutent name |
|---|---|---|
| 13 | | 3-dibenzothiophene |
| 14 | | terphenyl |
| 15 | | carbazolyl |

For example, No. 15 substituent in Table 1 is used as a substituent on a benzene ring P2 to form two stable blue phosphorescent materials as a host of the organic light emitting layer, that is, 3-carbazolyl-C-phenyl benzimidazolyl benzene (as illustrated in Formula 2) and 4-carbazolyl-C-phenyl benzimidazolyl benzene (as illustrated in Formula 3), which are called as mNBICz and pNBICz, respectively, for short:

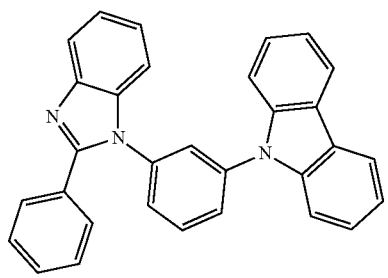

Formula 2

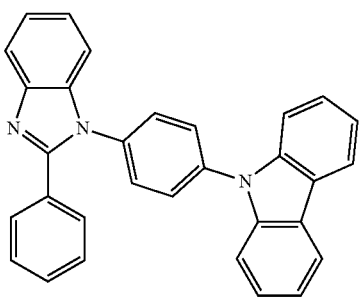

-continued

Formula 3

Below, the preparing processes of said benzimidazole derivatives mNBICz and pNBICz are introduced, the preparing methods for pNBICz and mNBICz are similar, and the preparation routes are as illustrated in Reaction scheme 1:

Reaction scheme 1

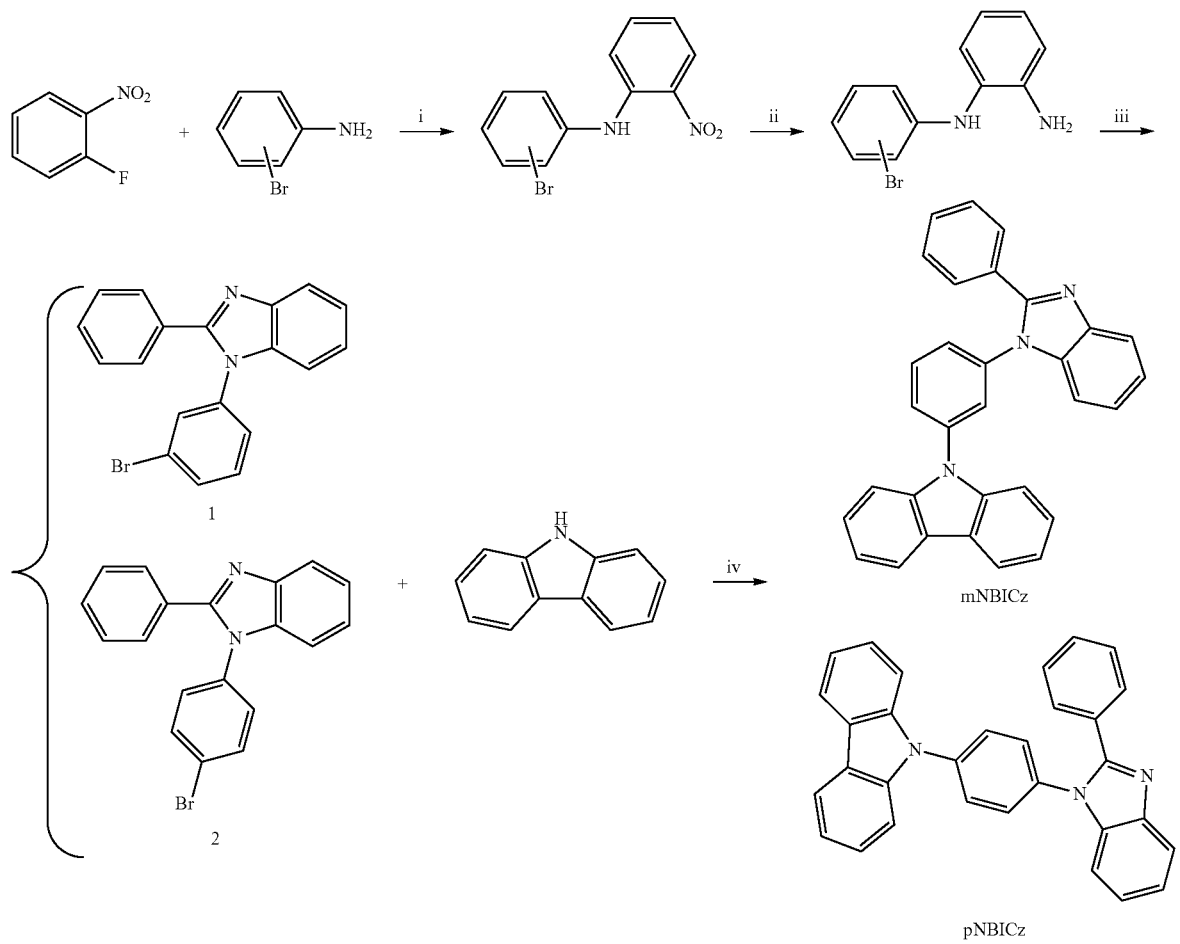

Particularly, the preparing steps of C-phenyl-1-p-bromophenyl benzimidazole, pNBICz, are taken as an example, as follows:

Step A: The Obtaining of 4-bromine-N-phenyl o-nitroaniline

In a dry round-bottom flask, a mixture of o-fluoronitrobenzene (4.40 g, 31.7 mmol), p-bromoaniline (10.9 g, 63.4 mmol) and anhydrous potassium fluoride (2.30 g, 39.6 mmol) are put therein, heated to 150° C. under the protection of nitrogen gas and reflux for 24 hours. After the reaction ends, the product is dissolved into dichloromethane and washed for three times with water, after being dried with anhydrous sodium sulfate, spin to dryness, the product is recrystallized with methanol, and 5.7 g of a final product of orange acicular crystal is obtained and the yield is 61%.

Physical and chemical parameters of the final product are: $^1$H NMR (400 MHz, CDCl$_3$, δ): 9.39 (s, 1H), 8.21 (d, J=7.6 Hz, 1H), 7.53 (d, J=7.6 Hz, 2H), 7.39 (t, J=12.4 Hz, 1H), 7.14-7.21 (m, 3H), 6.81 (t, J=12.4 Hz, 1H). MS (APCI): calcd for C$_{12}$H$_9$N$_2$O$_2$Br, 293.12; found, 294.4 (M+1)$^+$, from which it can be seen that the final product is 4-bromine-N-phenyl o-nitroaniline.

Step B: The Obtaining of N-(4-bromophenyl)-o-phenylenediamine

In a single port flask of 500 ml, the compound, 4-bromine-N-phenyl o-nitroaniline (5.70 g, 19.4 mmol), obtained in step A and a reductant, stannous chloride (22.0 g, 97.0 mmol) are dissolved with 250 ml of absolute ethanol, heated and reflux to be reacted overnight. After reaction ends, the solvent is evaporated to dryness. Then 500 ml of water is added, and the solution is adjusted to be neutral with sodium bicarbonate. Ethyl acetate is used for extraction for three times, an organic layer is dried with sodium sulfate, and then a solvent is evaporated to obtain 4.1 g of coarse product and the yield thereof is 80%.

Physical and chemical parameters of the coarse product are: $^1$H NMR (400 MHz, CDCl$^3$, δ): 7.28 (d, J=7.6 Hz, 2H), 7.01-7.10 (m, 2H), 6.73-6.82 (m, 2H), 6.60 (d, J=7.6 Hz, 2H), 5.18 (s, 1H), 3.75 (s, 2H). MS (APCI): calcd for C$_{12}$H$_{11}$N$_2$Br, 263.12; found, 264.3 (M+1)$^+$, from which it can be verified that N-(4-bromophenyl)-o-phenylenediamine is included.

Step C: The Obtaining of C-phenyl-1-p-bromophenyl benzimidazole

N-(4-bromophenyl)-o-phenylenediamine (4 g, 14.4 mmol) obtained in step B is dissolved into glacial acetic acid (100 ml), reacted overnight in a temperature of 120° C. and evaporated the glacial acetic acid therein to dryness to obtain 23.6 g of brown solid powder and the yield thereof is 98%. Physical and chemical parameters of the brown solid powder are: $^1$H-NMR (DMSO-d$_6$, 400 MHz): δ (ppm) 7.82~7.80 (d, J=7.6 Hz, 1H), 7.62~7.54 (m, 5H), 7.46~7.44 (m, 4H), 7.35~7.27 (m, 2H), 7.21~7.19 (d, J=7.2 Hz, 2H), from which it can be verified that the product is C-phenyl-1-p-bromophenyl benzimidazole.

Step D: the Obtaining of 4-carbazolyl-C-phenyl benzimidazolyl benzene (pNBICz)

In a dry flask of 50 ml, carbazole (1.5 g, 9 mmol), C-phenyl-1-p-bromophenyl benzimidazole (2.78 g, 8.0 mmol), cuprous iodide (0.046 g, 0.24 mmol), 18-crown ether-6 (0.064 g, 0.24 mmol) and potassium carbonate (5.53 g, 40.0 mmol) are dissolved into DMPU (2 ml), heated to 170° C., heated to 170° C. under the protection of nitrogen gas and reacted for two days. After filtration, an organic solvent and water are used respectively for washing, and finally 2.4 g of a white product is obtained by column chromatography and the yield thereof is 90%.

Physical and chemical parameters of the white product are: $^1$H-NMR(CDCl$_3$, 600 MHz): δ(ppm) 8.27~8.29 (m, 1H), 7.89~7.94 (dd, J=6 Hz, 3H), 7.65~7.68 (m, 2H), 7.44~7.45 (d, J=6 Hz, 1H), 7.25~7.28 (m, 1H), 7.01~7.10 (m, 5H), 6.82~6.89 (m, 4H), 6.76~6.78 (t, J=12 Hz, 2H), 6.30~6.31 (d, J=6 Hz, 2H). $^{13}$C-NMR (150 MHz, CDCl$_3$): δ 139.81, 136.34, 133.97, 131.18, 128.69, 128.31, 127.85, 127.74, 125.62, 124.46, 123.56, 123.26, 119.91, 119.41, 110.29, 109.83. MS (APCI): calcd for $C_{31}H_{21}N_3$, 435.17; found, 436.2 (M+1)$^+$. Anal. calcd for $C_{31}H_{21}N_3$ (%): C, 85.34, H, 4.93, N, 9.73; found: C, 85.90, H, 4.20, N, 9.90, from which it can be verified that 4-carbazolyl-C-phenyl benzimidazolyl benzene is included.

Similarly, step A (p-bromoaniline is replaced by m-bromoaniline, other reaction methods are the same) and step B are repeated, C-phenyl-1-m-bromophenyl benzimidazole is obtained in step C, and C-phenyl-1-m-bromophenyl benzimidazole is used to react with carbazole in step D to obtain a white product and the yield thereof is 88%.

Physical and chemical parameters of the white product are: $^1$H NMR (400 MHz, CDCl$_3$) δ (ppm): 7.98~8.00 (d, J=6 Hz 2H), 7.80~7.84 (d, J=6 Hz 1H), 7.70~7.75 (t, J=12 Hz 1H), 7.53~7.62 (m, 4H), 7.32~7.48 (m, 4H), 7.15~7.30 (m, 7H), 6.90~7.00 (s, 2H), $^{13}$C NMR (400 MHz, CDCl$_3$) δ [ppm]: 152.55, 142.93, 140.48, 139.52, 138.63, 136.81, 131.98, 130.30, 129.96, 129.67, 128.77, 126.67, 125.98, 125.08, 123.73, 123.37, 120.20, 120.05, 110.58, 109.55. MS (APCI): calcd for $C_{31}H_{21}N_3$, 435.17; found, 436.1 (M+1)$^+$. Anal. calcd for $C_{31}H_{21}N_3$ (%): C, 85.34, H, 4.93, N, 9.73; found: C, 85.40, H, 4.90, N, 9.70, from which it can be verified that 3-carbazolyl-C-phenyl benzimidazolyl benzene is included.

Figure 2:
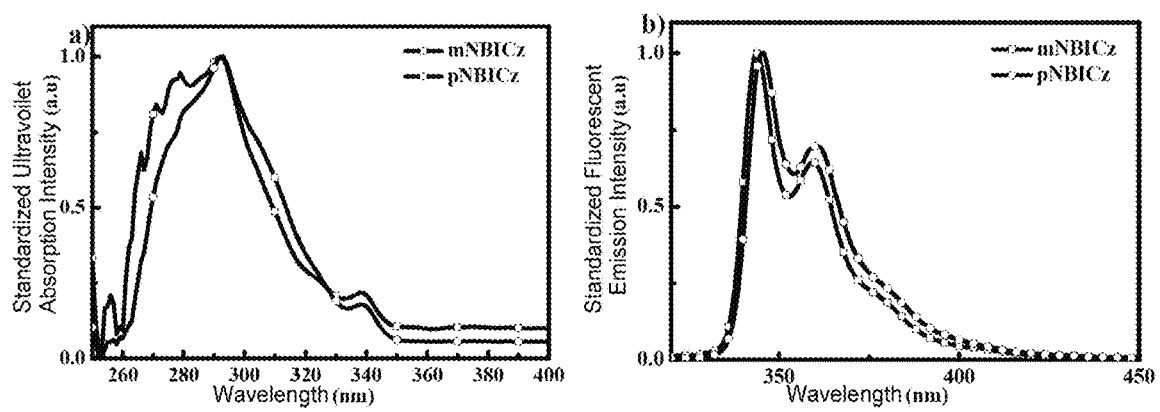
FIG. 2 is UV-Vis (a) and PL spectra (b) of mNBICz and pNBICz being in a toluene solution of embodiment 1 of the present invention.

Combining with FIG. 2, UV-Vis (a) and PL spectra (b) of mNBICz and pNBICz being in a toluene solution are shown. It may be calculated from FIG. 2 that the Egs of the two compounds are 3.57 eV (mNBICz) and 3.51 eV (pNBICz). Regarding PL spectra of mNBICz and pNBICz, the greatest emission peak is at 344 nm, and there is a shoulder peak at 360 nm, which explains that the two compounds both have intramolecular energy transfer in a certain degree.

Figure 3:
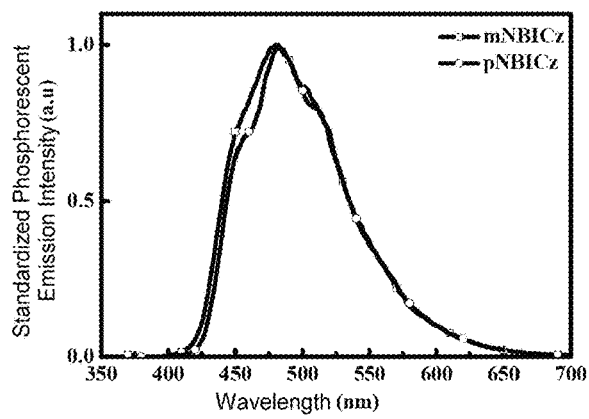
FIG. 3 is a low temperature phosphorescence emission spectra of mNBICz and pNBICz in 77K liquid nitrogen in embodiment 1 of the present invention.

Low temperature phosphorescence emission spectra of mNBICz and pNBICz in 77K liquid nitrogen are shown in FIG. 3. Their triplet energy levels may be calculated from the first emission peaks of the compounds, and a high-low order of the triplet energy levels is mNBICz (2.78 eV)>pNBICz (2.71 eV).

Below the process steps for preparing an organic light emitting device using the above two materials are introduced.

Two organic light emitting devices may be formed by using the above two materials, the host material is mNBICz, by which an organic light emitting device A is obtained; and the host material is pNBICz, by which an organic light emitting device B is obtained. Both two organic light emitting devices can be obtained using the following method: ITO glass is cleaned by ultrasonic wave for 30 minutes in a cleaning agent and deionized water in succession. Then the ITO glass is vacuum dried for 2 hours (105° C.), then put in a plasma reactor to be performed CFx plasma process for 1 minute and transferred into a vacuum chamber for preparing an organic film and a metal electrode. The mNBICz is prepared to be a device as the host material by the vacuum evaporation method.

Figure 4:
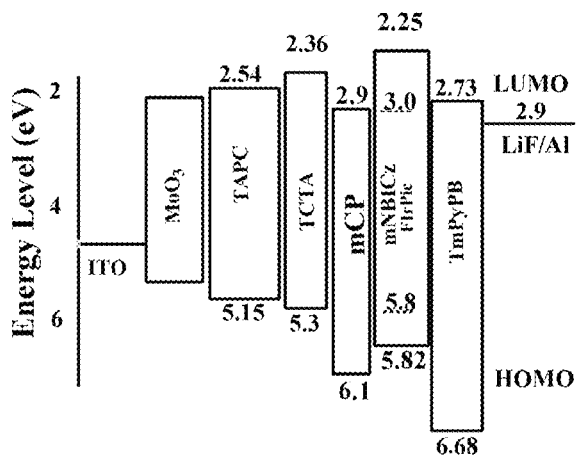
FIG. 4 is an energy level schematic diagram of respective compounds in organic light emitting devices A and B in embodiment 1 of the present invention.

Combining with FIG. 4, it can be seen from the energy level schematic diagrams of respective compounds of the organic light emitting devices A and B that the obtained structures of the two organic light emitting devices from the bottom to the top may be:

the organic light emitting device A: ITO/MoO$_3$ (thickness thereof is 10 nm)/NPB (thickness thereof is 40 nm)/mCP (thickness thereof is 5 nm)/Host: 6 wt % of FIrpic (thickness thereof is 20 nm)/TmPyPB (thickness thereof is 40 nm)/LiF (thickness thereof is 1 nm)/Al (thickness thereof is 100 nm), wherein the Host is mNBICz;

the organic light emitting device B: ITO/MoO$_3$ (thickness thereof is 10 nm)/NPB (thickness thereof is 40 nm)/mCP (thickness thereof is 5 nm)/Host: 6 wt % of FIrpic (thickness thereof is 20 nm)/TmPyPB (thickness thereof is 40 nm)/LiF (thickness thereof is 1 nm)/Al (thickness thereof is 100 nm), wherein the Host is pNBICz;

wherein 6 wt % indicates that the mass fraction that the amount of the dopant FIrpic occupies the host material Host is 6%.

Figure 5:
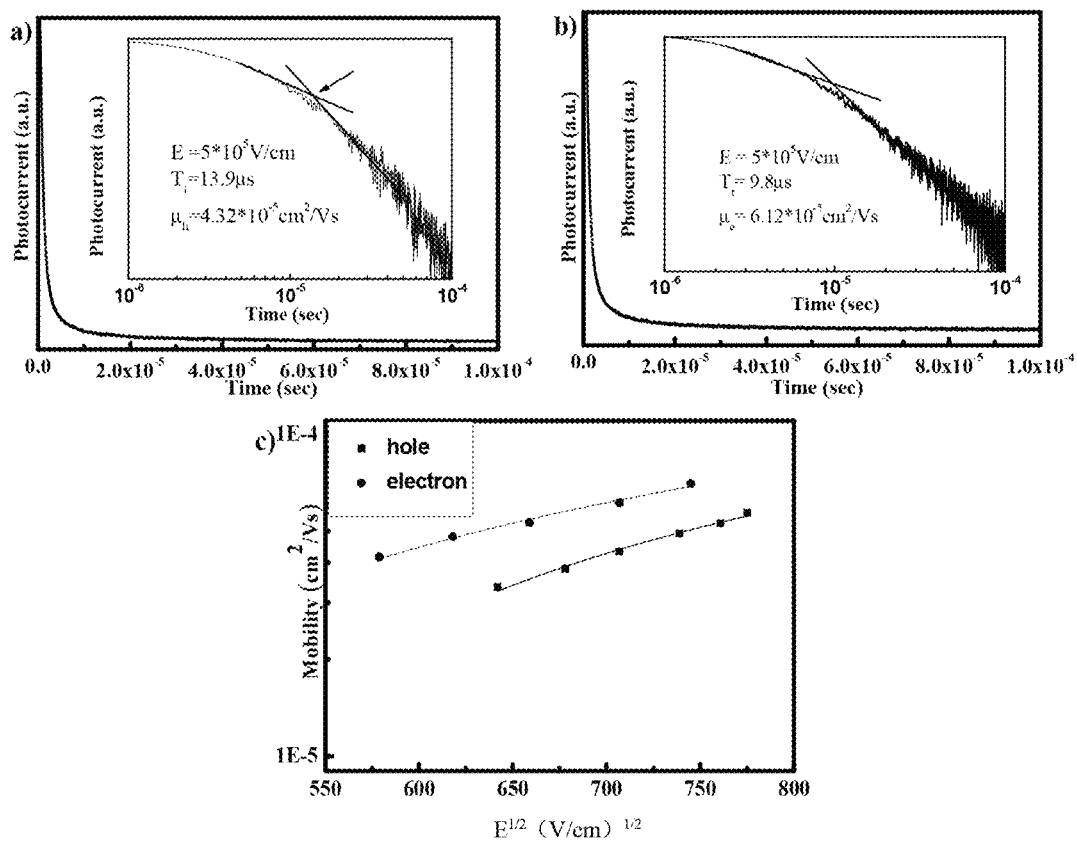
FIG. 5 is time spectral curves of mNBICz in embodiment 1 of the present invention: (a) hole; (b) electron; and (c) mobility curves of holes and electrons.

Combining with FIG. 5, it shows time spectral curves of mNBICz: (a) hole and (b) electron; and (c) mobility curves of holes and electrons. When an intensity of an electric field is $5.0 \times 10^5$ V cm$^{-1}$, the mobility of holes and electrons of mNBICz are $4.32 \times 10^{-5}$ cm$^2$ V$^{-1}$ s$^{-1}$ and $6.12 \times 10^{-5}$ cm$^2$ V$^{-1}$ s$^{-1}$, respectively. It can be seen from the figure that mobilities of electrons and holes of the mNBICz are similar under the same intensity of an electric field, which are both $10^{-5}$ magnitude, and the mobility of electrons is slightly higher than that of holes; in a case where an intensity of an electric field changes, mobilities of holes and electrons will also increase with an increase in the intensity of an electric field, but are maintained within a stable range in general and similar in numeral values. This explains that mNBICz has transport performances of holes and electrons at the same time, and the transport abilities for two carriers are similar, which is advantageous for the exciton to recombine at the center of the light emitting layer to emit light, thereby improving a recombination probability and quantum efficiency.

Figure 6:
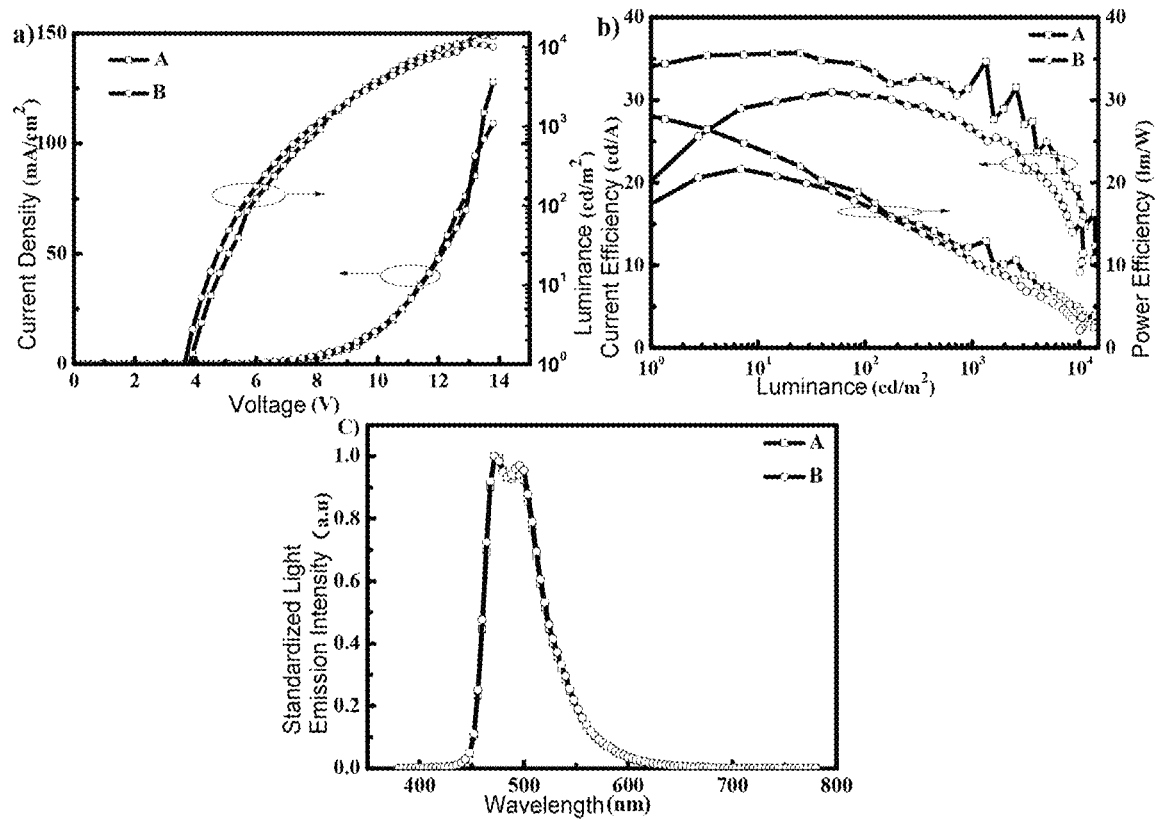
FIG. 6 is representations of electroluminescent devices of mNBICz and pNBICz in embodiment 1 of the present invention: (a) L-V-J curves; (b) efficiency-luminance relation graph; and (c) EL spectra.

FIG. 6 is representations of electroluminescent devices of mNBICz and pNBICz. (a) L-V-J curves, (b) efficiency-luminance relation graph and (c) EL spectra are shown. It can be seen from the device data in the above figure that mNBICz and pNBICz show good efficiencies in a evaporation device, the current efficiencies $\eta_{CE,max}$ reach to 35.7 and 30.9 cd/A, respectively, the power efficiencies $\eta_{PE,max}$ reach to 29.0 and 21.7 lm/W, respectively, and the external quantum efficiencies $EQE_{max}$ reach to 17.3% and 15.1%, respectively. From a light emitting efficiency, the phosphorescent host compound of benzoidazole in which N bits are substituted with carbazole is suitable for being used as a host material of a blue phosphorescent device of small molecule evaporation. More important, the roll-off of the two devices under a high current density are also comparatively small. It can be seen from the figure that emission peaks only occur at 476 nm and 500 nm in the electroluminescent spectra of mNBICz and pNBICz, which are characteristic emission peaks of the object material FIrpic. CIEs of the organic light emitting devices A and B under the voltage of 8V are both (0.15, 0.35) and both conform to color coordinate constants of a sky blue phosphorescence.

Embodiment 2

Figure 7:
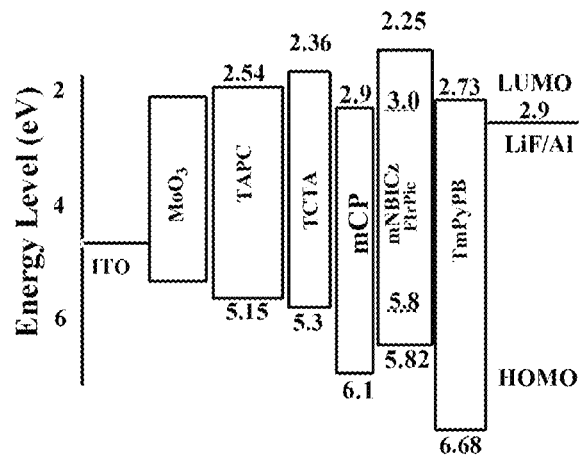
FIG. 7 is an energy level schematic diagram of respective compounds in organic light emitting devices C and D in embodiment 2 of the present invention.

The present embodiment further optimizes the structure of the organic light emitting device. Compared with the embodiment 1, in the organic light emitting device of the present embodiment, 4,4'-cyclohexyl di[N,N-di(4-methylphenyl)phenylamine] (TAPC) is used to replace NPB to be used as a hole transport layer, 4,4',4''-tris(carbazole-9-yl)triphenylamine (TCTA) is used as an exciton blocking layer, and a conventional phosphorescent material mCP is used for reference. Combining with FIG. 7, it can be seen from the energy level schematic diagrams of respective compounds of the organic light emitting devices C and D that the formed structures are as follows:

the organic light emitting device C: ITO/MoO$_3$ (10 nm)/TAPC (60 nm)/TCTA (5 nm)/Host: FIrpic (7 wt %, 20 nm)/TmPyPB (35 nm)/LiF (1 nm)/Al (100 nm), wherein the Host is mNBICz;

the organic light emitting device D: ITO/MoO$_3$ (10 nm)/TAPC (60 nm)/TCTA (5 nm)/Host: FIrpic (7 wt %, 20 nm)/TmPyPB (35 nm)/LiF (1 nm)/Al (100 nm). Wherein the Host is mCP;

Referring to Table 2, it illustrates performance parameters of organic light emitting devices A, B, C and D.

52.2 lm/W, respectively. A start voltage of the corresponding organic light emitting device D is 3.65V, the maximum luminance thereof is 9093 cd/m$^2$, the $EQE_{max}$ thereof is 13.3%, and the $\eta_{CE,max}$ and $\eta_{PE,max}$ thereof are 27.7 cd/A and 24.7 lm/W, respectively. The structure of the organic light emitting device C shows a more excellent quality.

Embodiment 3

The present embodiment further prepares a structure of a white light organic light emitting device having a single host complementary color based on a good blue light device efficiency of embodiment 2. Compared with embodiment 2, in the organic light emitting device of the present embodiment, the blue light object still adopts with FIrpic, the orange light object adopts with bis(2-phenyl-benzothiazole-C2,N)(acetylacetonate)iridium (III) (Ir(bt)2 (acac)), and the stability of the white light organic light emitting device is analyzed and evaluated by adjusting a doping concentration of the orange light object. The structures of the formed four organic light emitting devices E, F, G and H are as follows:

the organic light emitting device E:

ITO/MoO$_3$ (10 nm)/TAPC (60 nm)/TCTA (5 nm)/Host: FIrpic:Ir(bt)2(acac)

(7 wt %:0.5 wt %, 20 nm)/TmPyPB (35 nm)/LiF (1 nm)/Al; wherein the Host is mNBICz;

the organic light emitting device F:

ITO/MoO$_3$ (10 nm)/TAPC (60 nm)/TCTA (5 nm)/Host: FIrpic:Ir(bt)2(acac)

(7 wt %:1 wt %, 20 nm)/TmPyPB (35 nm)/LiF (1 nm)/Al; wherein the Host is mNBICz;

the organic light emitting device G:

ITO/MoO$_3$ (10 nm)/TAPC (60 nm)/TCTA (5 nm)/Host: FIrpic:Ir(bt)2(acac)

(7 wt %:1.5 wt %, 20 nm)/TmPyPB (35 nm)/LiF (1 nm)/Al; wherein the Host is mNBICz;

TABLE 2

Performance parameters of organic light emitting devices A, B, C and D

| Device | Host | $V_{on}(v)^a$ | $L_{max}$[cd/m$^2$] (V at $L_{max}$, V) | $\eta_c^b$[cd/A] | $\eta_p^b$[lm/W] | $EQE^b$ [%] | CIE [x, y]$^c$ |
|---|---|---|---|---|---|---|---|
| A | mNBICz | 3.3 | 13740 (13.8) | 35.7 | 29.0 | 17.3 | (0.15, 0.35) |
| B | pNBICz | 3.3 | 10070 (13.8) | 30.9 | 21.7 | 15.1 | (0.15, 0.35) |
| C | mNBICz | 3.31 | 47995 (11.9) | 54.5 | 52.2 | 26.2 | (0.14, 0.32) |
| D | mCP | 3.65 | 9093 (13.25) | 27.7 | 24.7 | 13.3 | (0.15, 0.14) |

$^a$$V_{on}$: Start voltage;
$L_{max}$: Maximum luminance;
V: Voltage at the maximum luminance;
$\eta_c$: Current efficiency;
$\eta_p$: Power efficiency;
CIE[x, y]: International color coordinates;
$^b$Maximum efficiency;
$^c$The measurement voltage is 8 V.

Figure 8:
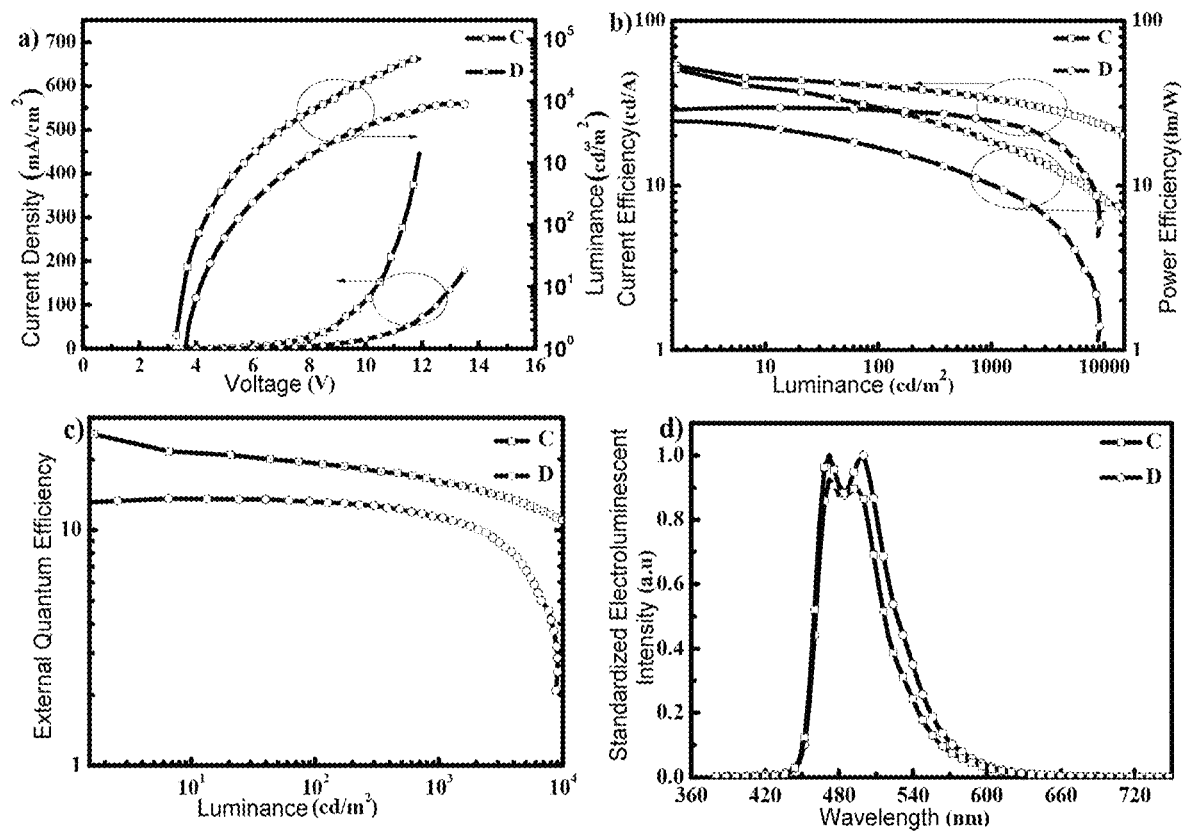
FIG. 8 is electroluminescent device data curves of organic light emitting devices C and D in embodiment 2 of the present invention: (a) L-V-J curves; (b) efficiency-luminance relation graph; (c) EQE and a luminance curve; and (d) EL spectra.

FIG. 8 shows electroluminescent device data curves of organic light emitting devices C and D: (a) L-V-J curves; (b) efficiency-luminance relation graph; (c) EQE and luminance curves; and (d) EL spectra. The start voltage of the organic light emitting device C is 3.3V, and the maximum light emitting luminance reaches to 47995 cd/m$^2$, which is measured when an operation voltage is 11.9V. Meanwhile, the $EQE_{max}$ of the organic light emitting device C reaches to 26.2%, and the $\eta_{CE,max}$ and the $\eta_{PE,max}$ are 54.5 cd/A and the organic light emitting device H:

ITO/MoO$_3$ (10 nm)/TAPC (60 nm)/TCTA (5 nm)/Host: FIrpic:Ir(bt)2(acac)

(7 wt %:2 wt %, 20 nm)/TmPyPB (35 nm)/LiF (1 nm)/Al; wherein the Host is mNBICz.

The present embodiment further analyzes the performances of the above four organic light emitting devices, as illustrated in Table 3:

TABLE 3

Device performance of the white light device of mNBICz

| device | $V_{on}$ (v)[a] | $L_{max}$[cd/m$^2$] (V at $L_{max}$, V) | $\eta_c{}^b$[cd/A] | $\eta_p{}^b$[lm/W] | EQE[b] [%] | CIE [x, y][c] |
|---|---|---|---|---|---|---|
| E | 3.32 | 48460(13.9) | 46.9/34.0 | 44.6/17.4 | 17.2 | (0.35, 0.44) |
| F | 3.32 | 48380 (12.5) | 54.7/45.7 | 48.7/23.4 | 17.5 | (0.39, 0.46) |
| G | 3.32 | 48202 (12.5) | 62.5/49.9 | 60.4/27.4 | 22.9 | (0.39, 0.45) |
| H | 3.32 | 48504 (12.5) | 55.3/47.7 | 52.7/24.7 | 20.0 | (0.44, 0.47) |

[a]$V_{on}$: Start voltage;
$L_{max}$: Maximum luminance;
V: Voltage at the maximum luminance;
$\eta_c$: Current efficiency;
$\eta_p$: Power efficiency;
CIE[x, y]: International color coordinates;
[b]Maximum efficiency;
[c]The measurement voltage is 8 V.

Figure 9:
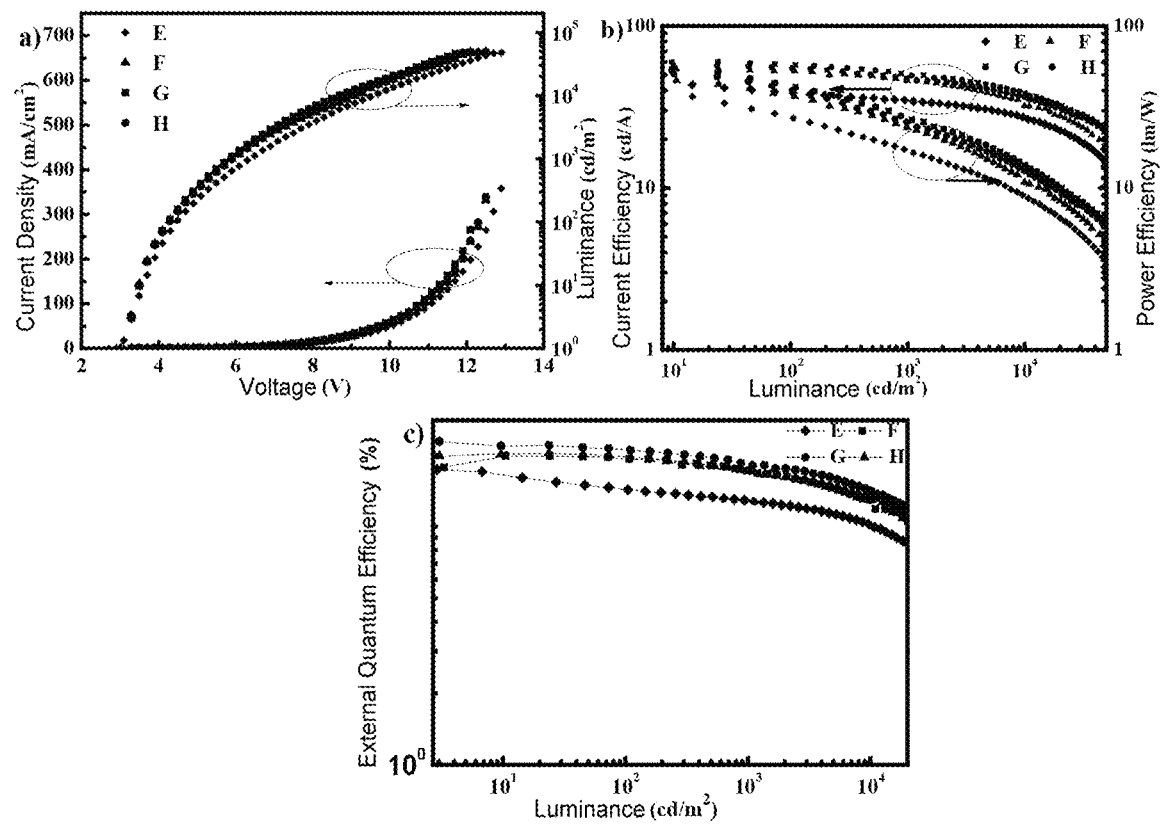
FIG. 9 is representations of a white light device of mNBICz in embodiment 3 of the present invention: (a) L-V-J curves; (b) efficiency and luminance; and (c) a luminance-external quantum efficiency curve, and the inserted images are EL spectra under different bias voltages.

As shown in FIG. 9, it can be seen from the spectrum data that the color of the light is gradually red shift with the increasing of the value of n. The light emitting efficiency of the organic light emitting device G is maximum, the $\eta_{CE,max}$ reaches to 62.5 cd/A, the $\eta_{PE,max}$ is 60.4 lm/W, the $EQE_{max}$ is 22.9%, and the start voltage is only 3.3V. Thus, it can be said that when doping concentration of Ir(bt)2(acac) is 1.5%, the performance is the optimal, but as the doping concentration changes, respective device efficiencies do not obviously change, which explains that respective device performances are stable. In addition, the maximum light emitting luminance of the four white light devices all exceed 48000 cd/m$^2$ and meet the requirements in actual applications. As same as the blue light device, matched bipolar transmission characteristic of the host material mNBICz plays a crucial role.

It can be further seen from FIG. 9 that the emission peak at 475 nm in the whole spectra is gradually strengthened with the increasing of the voltage. This is because the emission of the blue light portion, that is, the emission of the object FIrpic mainly comes from triplet energy transfer from the host to the object, while the emission of the orange light portion mainly comes from direct recombination luminescence of exciton on the object Ir(bt)$_2$(acac). According to reports from literatures, the increasing of the voltage is advantageous to the energy transfer from the host to the object, but not advantageous to direct exciton capturing of the object, such that this spectrum phenomenon occurs. Although the spectrum changes with the change of the voltage, the whole change is not great, with the operation voltages from 5V to 10V, the color rendering index (CRI) only changes from 60.3 to 62.4, it can be said that the light color is fully stable. In conclusion, the efficiency, the light emitting intensity and the stability of the spectrum of the white light device E-H all reach to a satisfactory level.

Embodiment 4

The present embodiment provides other preparing methods for benzimidazole derivatives as the materials of the organic light emitting layer.

For example, No. 14 substituent in Table 1 is used as a substituent on the benzene ring P2 to form three stable blue phosphorescent materials as a Host of the organic light emitting layer, as illustrated in Formulae 4, 5 and 6, and Formulae 4, 5 and 6 are called as oBITP, mBITP and pBITP, respectively, for short:

Formula 4

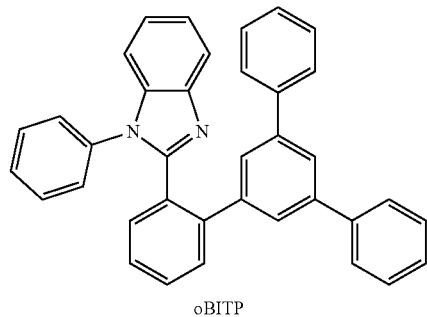

oBITP

Formula 5

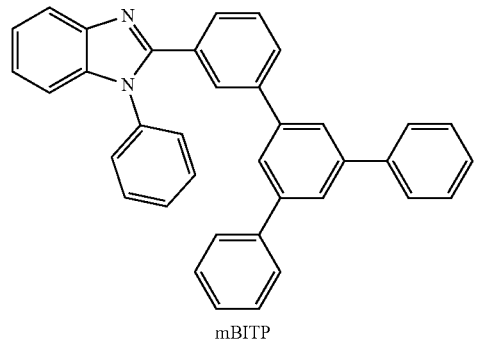

mBITP

Formula 6

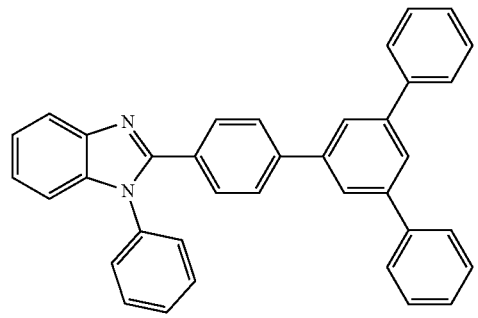

pBITP

Below, the preparing processes of said benzimidazole derivatives oBITP, mBITP and pBITP are introduced, the preparing methods for oBITP, mBITP and pBITP are similar, and the preparation routes are as illustrated in Reaction scheme 2:

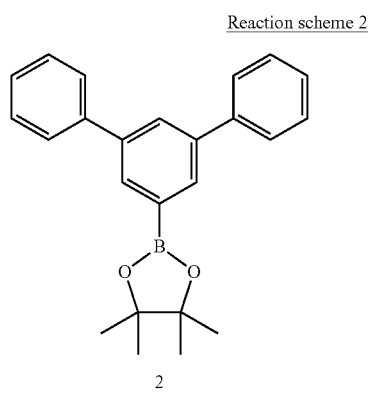

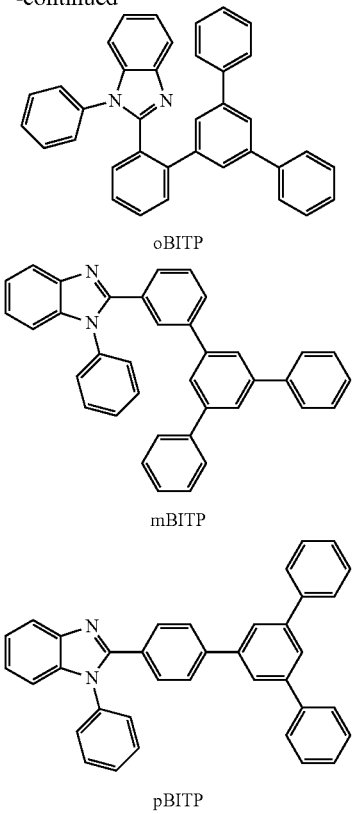

The preparing steps of mBITP are particularly taken as an example for specific description.

A. Synthesis of mBITP:

In a flask of 150 ml, 3-Bromophenylbenzimidazole (0.87 g, 2.5 mmol), 1-boric acid-m-terphenyl (2) (1.1 g, 4 mmol), Pd(PPh3)$_4$ (0.11 g, 0.1 mmol), potassium carbonate (2.0 M) (5.0 ml, 10.0 mmol), toluene (25 ml) and absolute ethanol (15 ml) are sequentially put therein. They are heated to 100° C. to react for 12 hours under the protection of nitrogen gas. After the reaction ends, they are cooled to a room temperature, an apparent layered phenomenon appears in the reaction system, the upper layer is yellow liquid and the lower layer is colorless transparent liquid. The liquid of the lower layer is removed, the solution of the upper layer is evaporated, and the obtained coarse product is purified through the method of column chromatography to obtain 0.98 g of white solid powder and the yield is 80%.

Physical and chemical parameters of the white solid powder are: $^1$H-NMR(CDCl$_3$, 400 MHz): δ(ppm) 7.91~7.93 (d, J=8 Hz, 1H), 7.75~0.7.81 (m, 3H), 7.63~7.70 (m, 5H), 7.34~7.55 (m, 14H), 7.28~7.29 (t, J=4 Hz, 3H). $^{13}$C-NMR (100 MHz, CDCl$_3$): δ 142.36, 141.38, 140.91, 137.11, 130.02, 129.08, 128.88, 128.77, 128.32, 127.62, 127.43, 125.41, 124.97, 119.87, 110.50. MS (APCI): calcd for C$_{37}$H$_{26}$N$_2$: 498.5, found, 499.6 (M+1)$^+$. Anal. calcd for C$_{37}$H$_{26}$N$_2$ (%): C, 89.13; H, 5.26; N, 5.62; found: C, 89.38, H, 5.11, N, 5.51.

B. Synthesis of oBITP:

The preparing process of oBITP is similar to that of mBITP, and a white solid powder is finally obtained by purification through column chromatography and the yield is 60%.

Physical and chemical parameters of the white solid powder are: $^1$H-NMR(CDCl$_3$, 400 MHz): δ(ppm) 7.99~8.18

(m, 2H), 7.53~7.58 (m, 3H), 7.37~7.46 (m, 2H), 6.91~7.28 (m, 17H), 6.52~6.54 (d, J=8 Hz, 2H). $^{13}$C-NMR (100 MHz, CDCl$_3$): δ 142.36, 141.38, 140.91, 130.02, 129.08, 128.88, 128.77, 128.32, 127.62, 127.43, 125.41, 124.97, 123.54, 123.17, 119.87, 110.50. MS (APCI): calcd for $C_{37}H_{26}N_2$: 498.4, found, 499.5 (M+1)$^+$. Anal. calcd for $C_{37}H_{26}N_2$ (%): C, 89.13; H, 5.26; N, 5.62; found: C, 89.08, H, 5.21, N, 5.71.

C. Synthesis of pBITP:

The preparing process of pBITP is similar to that of mBITP, and a white solid powder is finally obtained by purification through column chromatography and the yield is 86%.

Physical and chemical parameters of the white solid powder are:

$^1$H-NMR(CDCl$_3$, 400 MHz): δ(ppm) 7.90~7.92 (d, J=8 Hz, 1H), 7.76~7.77 (d, J=4 Hz, 3H) 7.63~7.70 (m, 8H), 7.45~7.55 (m, 7H), 7.33~7.40 (m, 5H), 7.24~7.27 (m, 2H). $^{13}$C-NMR (100 MHz, CDCl$_3$): δ151.99, 143.03, 142.49, 141.95, 141.19, 141.00, 137.38, 137.08, 129.99, 129.91, 128.87, 128.70, 127.63, 127.53, 127.35, 127.12, 125.65, 125.01, 123.44, 123.10, 119.85, 110.48. MS (APCI): calcd for $C_{37}H_{26}N_2$: 498.7, found, 499.8 (M+1)$^+$. Anal. calcd for $C_{37}H_{26}N_2$ (%): C, 89.13; H, 5.26; N, 5.62; found: C, 88.93; H, 5.16; N, 5.91.

Figure 11:
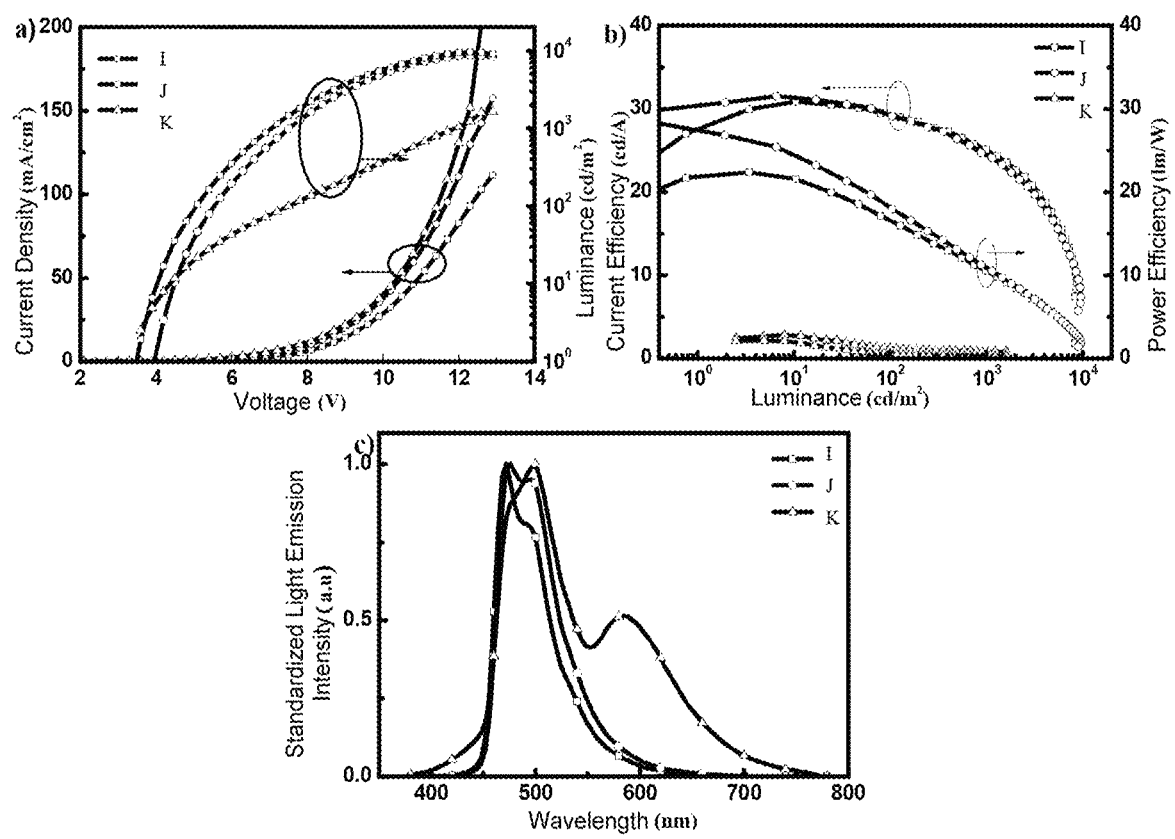
FIG. 11 is representations of devices of blue phosphorescent host materials oBITP, mBITP and pBITP in embodiment 4 of the present invention: (a) L-V-J curves of phosphorescent devices; (b) efficiency and luminance relation graphs in phosphorescent devices; and (c) EL spectra of phosphorescent devices.

The process steps for preparing an organic light emitting device using the above three materials may be referred to embodiment 1.

thereof is 20 nm)/TmPyPB (thickness thereof is 40 nm)/LiF (thickness thereof is 1 nm)/Al (thickness thereof is 100 nm), wherein Host is pBITP;

FIG. 11 shows representations of devices of blue phosphorescent host materials oBITP, mBITP and pBITP: (a) L-V-J curves of phosphorescent devices; (b) efficiency and luminance relation graphs in phosphorescent devices; and (c) EL spectra of phosphorescent devices. The start voltages of the three devices are 3.3, 3.6 and 3.6V, respectively. The organic light emitting devices I and J show good efficiencies under a evaporation condition, $\eta_{CE,max}$ reach to 30.1 cd/A and 31.5 cd/A, respectively, $\eta_{PE,max}$ reach to 22.4 and 28.4 lm/W, respectively, and $EQE_{max}$ reach to 16% and 14.7%, respectively. But the efficiency of the organic light emitting device K is very low, this may be because the electron injection energy barrier thereof is comparatively large, and meanwhile the triplet energy level is comparatively low, so that the exciton cannot be effectively limited in the light emitting layer. The HOMO and LUMO energy levels of oBITP are relatively similar to those of mBITP, and their triplet energy levels are both higher than 2.80 eV, which may preferably implement energy transfer between a host and an object as host materials. This explains that oBITP and mBITP are more suitable for being used as blue phosphorescent host materials by contrast with pBITP.

The present embodiment analyzes the performances of the organic light emitting devices prepared by oBITP, mBITP and pBITP as the host materials, and the result is illustrated in Table 4.

TABLE 4

Performances of the organic light emitting devices prepared by oBITP, mBITP and pBITP as host materials

| Device | Host | Von (v)a | Lmax[cd/m2] (V at Lmax, V) | ηcb[cd/A] | ηpb[lm/W] | EQEb[%] | CIE [x, y]c |
|---|---|---|---|---|---|---|---|
| I | oBITP | 3.3 | 9031 (12.9) | 30.1 | 22.4 | 16 | (0.14, 0.30) |
| J | mBITP | 3.6 | 8330 (12.9) | 31.5 | 28.4 | 14.7 | (0.15, 0.36) |
| K | pBITP | 3.6 | 1638 (12.9) | 2.82 | 2.23 | 1.1 | (0.30, 0.40) | aVon: Start voltage;
Lmax: Maximum luminance;
V: Voltage at the maximum luminance;
ηc: Current efficiency;
ηp: Power efficiency;
CIE[x, y]: Internation color coordinates;
bMaximum efficiency;
cThe measurement voltage is 8 V.

Figure 10:
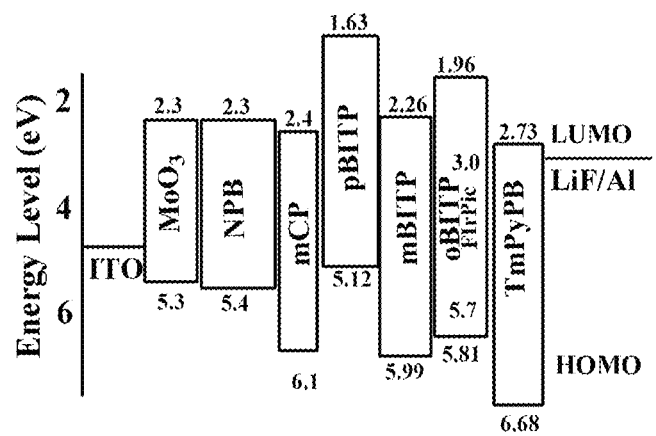
FIG. 10 is an energy level schematic diagram of respective compounds in organic light emitting devices I, J and K in embodiment 4 of the present invention.

Combining with FIG. 10, it can be seen from the energy level schematic diagrams of respective compounds of the organic light emitting devices I, J and K that the obtained structures of three organic light emitting devices from the bottom to the top are:

the organic light emitting device I: ITO/MoO$_3$ (thickness thereof is 10 nm)/NPB (thickness thereof is 40 nm)/mCP (thickness thereof is 5 nm)/Host: 6 wt % of FIrpic (thickness thereof is 20 nm)/TmPyPB (thickness thereof is 40 nm)/LiF (thickness thereof is 1 nm)/Al (thickness thereof is 100 nm), wherein Host is oBITP;

the organic light emitting device J: ITO/MoO$_3$ (thickness thereof is 10 nm)/NPB (thickness thereof is 40 nm)/mCP (thickness thereof is 5 nm)/Host: 6 wt % of FIrpic (thickness thereof is 20 nm)/TmPyPB (thickness thereof is 40 nm)/LiF (thickness thereof is 1 nm)/Al (thickness thereof is 100 nm), wherein Host is mBITP;

the organic light emitting device K: ITO/MoO$_3$ (thickness thereof is 10 nm)/NPB (thickness thereof is 40 nm)/mCP (thickness thereof is 5 nm)/Host: 6 wt % of FIrpic (thickness It may be further demonstrated according to Table 4 that: the EL spectra of organic light emitting devices I and J both present good emission peaks of the object FIrpic, the CIE coordinates are (0.14, 0.30) and (0.15, 0.36), respectively, and the devices maintain stably under different voltages, which verify that the triplet exciton of the two materials can be completely transferred to the object material from the result. Regarding pBITP, compared with the previous two compounds, since the conjugation degree formed between two para-connected benzenes is comparatively large, such that the triplet energy level is only 2.72 eV, which is only slightly higher than the triplet energy level of the object FIrpic, and thus complete transfer of the triple energy cannot be ensured. It can be seen from the EL spectrum of the organic light emitting device K that there is one more shoulder peak at 600 nm in addition to the emission peak of the object FIrpic, which explains that transfer of the triplet exciton between the host and the object is not well implemented, and the recombination area of the electron hole is not at the center of the light emitting layer, thereby further resulting in low device efficiency.

Although the present invention is shown and described with reference to the particular embodiments, those skilled in the art will understand: various changes in forms and details may be made therein without departing from the spirit and scope of the invention defined in claims and its equivalents.

The invention claimed is:

1. An organic light emitting device, comprising from the bottom to the top: a substrate, an anode layer, a hole injection layer, a hole transport layer, an exciton blocking layer, an organic light emitting layer, an electron transport layer, an electron injection layer and a cathode layer; wherein the organic light emitting layer includes benzimidazole derivative as illustrated in Formula 1,

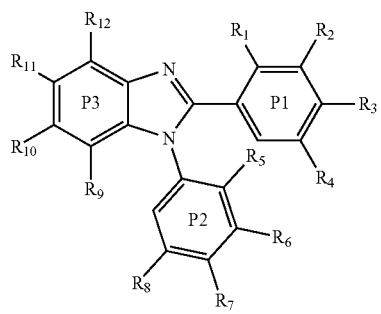

Formula 1 wherein P1, P2 and P3 are benzene rings, and at least one of $R_1$-$R_{12}$ is a substituent having hole transport ability, and wherein each of $R_1$-$R_{12}$ is selected from the group consisting of a hydrogen group, a phenyl group, a p-tolyl, a biaza-9-carbazolyl, a triphenyl silyl, a p-triphenylamino, a 1-naphthalene substituted p-triphenylamino, a 2-naphthalene substituted p-triphenylamino, a 3,6-ditert-butyl carbazolyl phenyl, a di3, 6-ditert-butyl carbazolyl phenyl, a p-triphenylamino, a 1-naphthalene substituted p-triphenylamino, a 2-naphthalene substituted p-triphenylamino, a 2-dibenzothiophene, a 3-dibenzothiophene, a 4-dibenzothiophene and a m-terphenyl.

2. The organic light emitting device of claim 1, wherein the organic light emitting layer further includes a dopant which is bis(4,6-difluorophenylpyridinato-N, C2)picolinatoiridium, or bis(2-phenyl-benzothiazole-C2,N)(acetylacetonate)iridium (III); and the mass fraction that the dopant occupies the organic light emitting layer is 0.5-7 wt %.

3. The organic light emitting device of claim 2, wherein the mass fraction that is the dopant bis(2-phenyl-benzothiazole-C2,N)(acetylacetonate)iridium (III)) occupies the organic light emitting layer is 0.5-5 wt %.

4. The organic light emitting device of claim 1, wherein the material of the anode layer is a semiconductor conducting film; the material of the hole injection layer is molybdenum oxide; the material of the hole transport layer is N,N'-diphenyl-N,N'-(1-naphthyl)-1,1'-biphenyl-4,4'-di- amine or 4,4'-cyclohexyl di[N,N'-di(4-methylphenyl)phenylamine]; the material of the exciton blocking layer is N,N'-dicarbazole-3,5-benzene or a 4,4',4''-tris(carbazole-9-yl)triphenylamine; the material of the electron transport layer is 1,3,5-tris[(3-pyridinyl)-3-phenyl]benzene; the material of the electron injection layer is LiF; and the cathode layer is Al.

5. A preparing method for an organic light emitting device, comprising:

forming an anode layer on a substrate;

sequentially forming a hole injection layer, a hole transport layer and an exciton blocking layer on the anode layer using a vacuum thermal evaporation method;

forming an organic light emitting layer which comprises benzimidazole derivative as illustrated in Formula 1 on the exciton blocking layer using a vacuum thermal evaporation method,

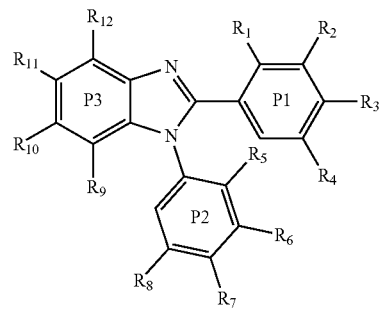

Formula 1 wherein P1, P2 and P3 are benzene rings, and at least one of $R_1$-$R_{12}$ is a substituent having hole transport ability, and wherein each of $R_1$-$R_{12}$ is selected from the group consisting of a hydrogen group, a phenyl group, a p-tolyl, a biaza-9-carbazolyl, a triphenyl silyl, a p-triphenylamino, a 1-naphthalene substituted p-triphenylamino, a 2-naphthalene substituted p-triphenylamino, a 3,6-ditert-butyl carbazolyl phenyl, a di3, 6-ditert-butyl carbazolyl phenyl, a p-triphenylamino, a 1-naphthalene substituted p-triphenylamino, a 2-naphthalene substituted p-triphenylamino, a 2-dibenzothiophene, a 3-dibenzothiophene, a 4-dibenzothiophene and a m-terphenyl; and forming an electron transport layer, an electron injection layer and a cathode layer on the organic light emitting layer using a vacuum thermal evaporation method.

6. The preparing method for an organic light emitting device of claim 5, wherein the organic light emitting layer further comprises a dopant which is bis(4,6-difluorophenylpyridinato-N, C2)picolinatoiridium, or bis(2-phenyl-benzothiazole-C2,N)(acetylacetonate)iridium (III); and the mass fraction that the dopant occupies the organic light emitting layer is 0.5-7 wt %.

* * * * *